United States Patent [19]

Tóth et al.

[11] Patent Number: 5,132,303

[45] Date of Patent: * Jul. 21, 1992

[54] 4-METHYLENE-2-OXO-8-AZASPIRO[4,5]-DECANE DERIVATIVES, PHARMACEUTICAL COMPOSITIONS CONTAINING THEM AND PROCESS FOR PREPARING SAME

[75] Inventors: Edit Tóth; József Törley; Sándor Gorog; László Szporny; Béla Kiss; Éva Pálosi; Dóra Groó; István Laszlovszky; Erzsébet Lapis; Ferenc Auth; László Gaál, all of Budapest, Hungary

[73] Assignee: Richter Gedeon Vegyeszeti Gyar Rt., Budapest, Hungary

[*] Notice: The portion of the term of this patent subsequent to Jun. 2, 2009 has been disclaimed.

[21] Appl. No.: 566,278

[22] Filed: Aug. 10, 1990

[30] Foreign Application Priority Data

Aug. 10, 1989 [HU] Hungary .................. 4094/89

[51] Int. Cl.$^5$ .................. A61K 31/44; C07D 471/10
[52] U.S. Cl. .................. 514/278; 546/19
[58] Field of Search .................. 546/19; 514/278

[56] References Cited

U.S. PATENT DOCUMENTS 3,399,192  8/1968  Regnier .................. 546/19

OTHER PUBLICATIONS

Jones et al., "Substituted 1,1,diphenyl . . . " J. Med. Chem. 14(2) 161–164 (1971).

Primary Examiner—Jane T. Fan
Assistant Examiner—Celia Chang
Attorney, Agent, or Firm—Herbert Dubno; Jonathan Myers

[57] ABSTRACT

The invention relates to novel, therapeutically active 4-methylene-2-oxo-8-azaspiro[4,5]decane derivatives of the compound,

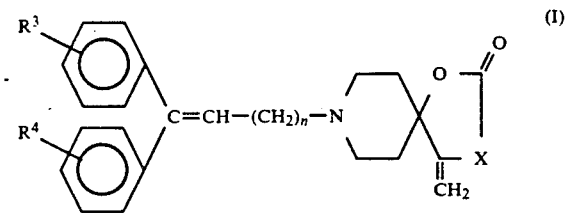

wherein
X means oxygen or an >NR group, wherein
  R stands for hydrogen, $C_{1-12}$alkyl, $C_{3-6}$cycloalkyl, carbocyclic $C_{6-10}$aryl or carbocyclic $C_{6-10}$aryl$C_{1-4}$alkyl group, the latter two being optionally substituted on their aromatic moiety by one or more, same or different halogen(s) or one or more $C_{1-4}$alkyl group(s) or by one or more $C_{1-4}$alkoxy group(s);
$R^3$ and $R^4$, which are the same or different, represent hydrogen, one or more halogen(s), $C_{1-4}$alkyl, $C_{1-4}$alkoxy, trihalomethyl group or hydroxyl group optionally esterified by a $C_{1-4}$alkanoic acid; and
$n$ is 1 or 2, their isomers, solvates, hydrates, acid addition and quaternary ammonium salts.

6 Claims, No Drawings

4-METHYLENE-2-OXO-8-AZASPIRO[4,5]DECANE DERIVATIVES, PHARMACEUTICAL COMPOSITIONS CONTAINING THEM AND PROCESS FOR PREPARING SAME

The invention relates to novel, therapeutically active 4-methylene-2-oxo-8-azaspiro[4,5]decane derivatives of the formula (I),

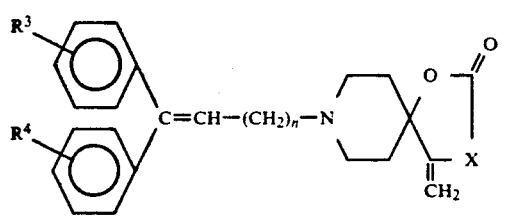

wherein
X means oxygen or an >NR group, wherein
R stands for hydrogen, $C_{1-12}$alkyl, $C_{3-6}$cycloalkyl, carbocyclic $C_{6-10}$aryl or carbocyclic $C_{6-10}$aryl-$C_{1-4}$alkyl group, the latter two being optionally substituted on their aromatic part by one or more, same or different halogen(s) or by one or more $C_{1-4}$alkyl group(s) or by one or more $C_{1-4}$alkoxy group(s);
$R^3$ and $R^4$, which are the same or different, represent hydrogen, one or more halogen(s), $C_{1-4}$alkyl, $C_{1-4}$alkoxy, trihalomethyl group or hydroxyl group optionally esterified by a $C_{1-4}$alkanoic acid; and
n is 1 or 2,
their isomers, solvates, hydrates, acid addition and quaternary ammonium salts as well as pharmaceutical compositions containing these compounds.

The invention also relates to a process for the preparation of the above compounds and compositions as well as to a method of treatment. The latter comprises administering a therapeutically effective amount of a compound of the formula (I) or a pharmaceutically acceptable acid addition or quaternary ammonium salt thereof to a patient for influencing the psychotic functions.

The compounds of the formula (I) may exist in various stereoisomeric forms such as geometrical isomers as well as racemates, individual (separated) optical isomers and their mixtures, all of which may occur in the form of various solvates and hydrates. All these compounds and mixtures are within the scope of the invention.

A number of therapeutically useful 2-oxo-1-oxa-3,8-diazaspiro[4,5]decane derivatives have been described in the literature. Such compounds are reported e.g. in the following publications: C.A. 71, 91359d (1969); C.A. 78, 23876q (1973); C.A. 81, 33153c and 105368b (1974); C.A. 95, 161765e (1981); as well as in the DE patent specifications Nos. 2,013,729, 2,013.668 and 2.163,000 and in the BE patent specifications Nos. 775,984, 774,170, 786,631 and 825,444; in the GB patent specification No. 1,100,281; in the published NL patent specification No. 7,214,689; as well as in the U.S. Pat. Nos. 3,555,033, 3,594,386, 4,244,961 and 4,255,432.

A substantial difference between the compounds of formula (I) according to the invention and similar derivatives known up to the present appears in the nature of the substituents bound in position 4 and optionally in position 3 of the spirodecane skeleton.

According to an other aspect of the invention, there is provided a process for the preparation of the compounds of the formula (I) as well as their acid addition and quaternary ammonium salts, which comprises a) reacting a 2-oxo-3,8-diazaspiro[4,5]decane derivative of the formula (II),

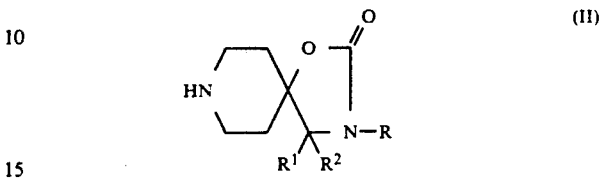

wherein R is as defined above and $R^1$ as well as $R^2$ together stand for a methylene group, with a diphenylalkene derivative of the formula (III),

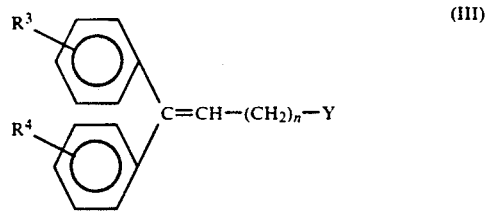

wherein $R^3$, $R^4$ and n are as defined above and Y means halogen, $C_{1-4}$alkylsulfonyloxy or arylsulfonyloxy group, to obtain compounds of the formula (I), wherein X stands for an >NR group and R, $R^3$, $R^4$ as well as n are as defined above; or b) reacting a 4-ethynyl-4-hydroxypiperidine derivative of the formula (IV),

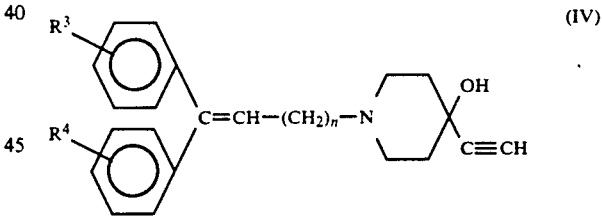

wherein $R^3$, $R^4$ and n are as defined above, with an isocyanate of the formula R—NCO, wherein R is as defined above, except hydrogen, then i) cyclizing the thus-obtained 4-carbamoyloxy-4-ethynylpiperidine derivative of the formula (V),

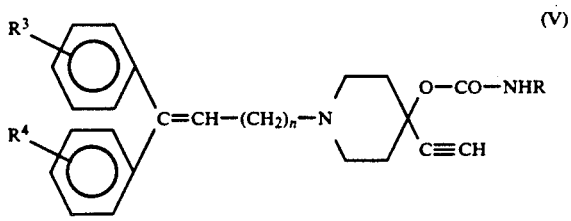

wherein R, $R^3$, $R^4$ and n are as defined above, in an acidic medium and reacting the 2-imino-1,3-dioxolane derivative of the formula (VI),

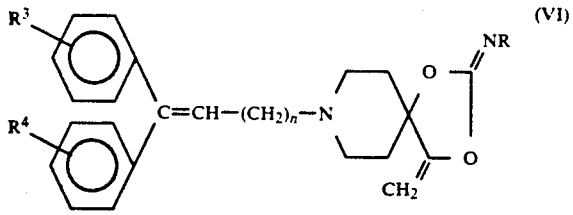

obtained in a salt form, wherein R, $R^3$, $R^4$ and n are as defined above, with water to obtain compounds of the formula (I), wherein X stands for oxygen and $R^3$, $R^4$ as well as n are as defined above; or ii) cyclizing the thus-obtained 4-carbamoyloxy-4-ethynylpiperidine derivative of the formula (V), wherein R, $R^3$, $R^4$ and n are as defined above, in a basic medium to obtain compounds of the formula (I), wherein X stands for an >NR group and R, $R^3$, $R^4$ as well as n are as defined above; or c) cyclizing a 4-carbamoyloxy-4-ethynylpiperidine derivative of the formula (V), wherein R, $R^3$, $R^4$ and n are as defined above for the formula (V), in an acidic medium and reacting the 2-imino-1,3-dioxolane derivative of the formula (VI) obtained in a salt form, wherein R, $R^3$, $R^4$ and n are as defined above, with water to obtain compounds of the formula (I), wherein X stands for oxygen and $R^3$, $R^4$ as well as n are as defined above; or d) cyclizing a 4-carbamoyloxy-4-ethynylpiperidine derivative of the formula (V), wherein R, $R^3$, $R^4$ and n are as defined above for the formula (V), in the presence of a base to obtain compounds of the formula (I), wherein X stands for an >NR group and R, $R^3$, $R^4$ as well as n are as defined above; or e) dehydrating a 2-oxo-1-oxa-8-azaspiro[4,5]decane derivative of the formula (VII),

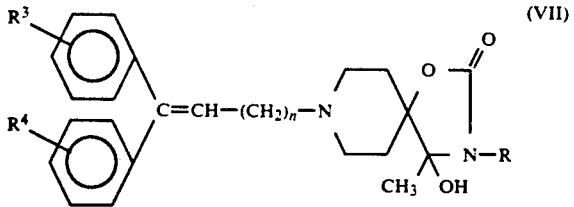

wherein R, $R^3$, $R^4$ and n are as defined for the formula (I), then, if desired, transforming a functional group of a thus-obtained compound of the formula (I), wherein X, R, $R^3$, $R^4$ and n are as defined for the formula (I), to an other one in a known manner, and/or reacting a thus-obtained compound of the formula (I), wherein X, R, $R^3$, $R^4$ and n are as defined above, with an acid to give an acid addition salt and/or treating a compound of the formula (I), wherein X, R, $R^3$, $R^4$ and n are as defined above, obtained as a salt, with a base to liberate the free basic form thereof and/or converting a thus-obtained compound of the formula (I), wherein X, R, $R^3$, $R^4$ and n are as defined above, to its quaternary ammonium salt.

In the process a) according to the invention a 2-oxo-3,8-diazaspiro[4,5]decane derivative of the formula (II) is reacted with a diphenylalkene derivative of the formula (III), wherein Y means e.g. a mesyloxy or tosyloxy group or a halogen, preferably chlorine or bromine.

This reaction is preferably accomplished in an inert organic solvent in the presence of a base being capable of binding the acid liberated in the reaction. Suitable solvents are e.g. aliphatic alkanols such as ethanol, isopropanol or butanol; aromatic hydrocarbons such as chlorobenzene or toluene; ethers such as dibutyl ether or dioxane; tertiary aliphatic acid amides such as dimethylformamide, dimethylacetamide; ketones such as acetone, methyl ethyl ketone or methyl isobutyl ketone; but a mixture of the above solvents may be employed, too. For binding the acid liberated in the reaction, inorganic or tertiary organic bases, e.g. carbonates or hydrogen carbonates of alkaline metals or alkaline earth metals as well as organic bases, e.g. triethylamine, dimethylaniline or pyridine may be used; though an excess of the compound of the formula (II) is also suitable for this purpose. This reaction may be carried out between room temperature and the boiling point of the reaction mixture; optionally, a catalyst may also be added. Suitable catalysts are alkaline metal iodides. It is preferable to work under an inert gas such as nitrogen or argon.

According to the process b) of the invention a 4-ethynyl-4-hydroxypiperidine derivative of the formula (IV) is first brought into reaction with an isocyanate of the formula R—NCO in a known manner (Houben-Weyl: Methoden der Organischen Chemie, Vol. VIII/3, page 137 to 147 (1952)) X to give a 4-carbamoyloxy-4-ethynylpiperdine derivative of the formula (V). According to step i) the thus-obtained compound of the formula (V) is cyclized in an acidic medium and the 2-imino-1,3-dioxolane derivative of the formula (VI) obtained as a salt is reacted with water to give compounds of the formula (I), wherein X means oxygen; or, according to step ii), the thus-obtained compound of the formula (V) is cyclized in a basic medium to obtain compounds of the formula (I), wherein X stands for an >NR group.

The cyclization according to step i) is carried out in an inert organic solvent (i.e. in a solvent which is inert under the reaction conditions), in the presence of a suitable acid, peferably in the presence of a dry hydrogen halide. Aliphatic or alicyclic ethers such as diethyl ether, dipropyl ether, diisopropyl ether, dibutyl ether, tetrahydrofuran or dioxane as well as lower aliphatic carboxylic acids, e.g. acetic or propionic acid, may be employed as solvents.

As a hydrogen halide hydrogen chloride, bromide, iodide or fluoride, preferably hydrogen chloride or bromide are used. After treating with water the thus formed 2-imino-1,3-dioxolane hydrohalide salt, the 4-methylene-2-oxo-8-azaspiro[4,5]decane derivative of the formula (I) is obtained as an acid addition salt, from which, if desired, the base can be liberated in a manner known per se.

The cyclization according to step ii) is carried out in the presence of a base. Alkaline metal acetates, carbonates, alkoxides, hydroxides and/or tertiary organic bases, e.g. pyridine, tripropylamine or picoline, may be used as basic catalysts in the cyclization; the organic bases may also serve as solvents for the reaction. Further suitable solvents are e.g. aliphatic alcohols such as methanol, ethanol, propanol or butanol; aliphatic, alicyclic or aromatic hydrocarbons such as methylene chloride, hexane, cyclohexane, benzene, toluene or xylene; acid amides such as dimethylformamide or N-methylpyrrolidone; ethers such as dibutyl ether or dioxane; nitriles such as acetonitrile; sulfoxides, e.g. dimethyl sulfoxide; as well as mixtures of the above solvents. The reaction may be carried out without any solvent, too, e.g. in molten state. In order to accelerate the cyclization the temperature is suitably increased: the reaction is preferably accomplished between 40° C. and the boiling point of the reaction mixture. It is suitable to work under an inert gas such as argon or nitrogen. According to a preferred embodiment, the 4-carbamoyloxy-4-ethynylpiperidine derivative of the formula (V) obtained from the reaction of 4-ethynyl-4-hydroxypiperidine derivative of the formula (IV) with the isocyanate of the formula R-NCO is not isolated but directly cyclized in the same reaction mixture in the presence of a suitable base.

In the case of processes c) and d) of the invention the procedures discussed under steps i) and ii) are followed.

In the case of process e) according to the invention a 2-oxo-1-oxa-8-azaspiro[4,5]decane derivative of the formula (VII) is dehydrated. The dehydration may be realized under atmospheric or reduced pressure by using procedures commonly known from the literature. Isocyanates, aliphatic carboxylic acids, aliphatic or aromatic carboxylic acid anhydrides, Lewis acids, sulfuric acid or aromatic sulfonic acids can be employed for dehydration. This reaction is preferably performed in an organic solvent. Suitable solvents are e.g. aromatic hydrocarbons such as benzene, toluene or xylene; ethers such as dioxane or di-n-butylether; or aliphatic carboxylic acids such as acetic acid. Optionally, the water formed in the reaction may azeotropically be distilled off.

If desired, the compounds of the formula (I) obtained by using the processes a) to e) can be transformed in a known way to other compounds being within the scope of the scope of the formula (I).

If desired, the compounds of the formula (I) may be converted to the acid addition and quaternary ammonium salts by using know methods. For the preparation of acid addition salts inorganic or organic acids such as hydrogen halides, e.g. hydrochloric acid or hydrobromic acid; sulfuric acid, phosphoric acids as well as formic, acetic, propionic, oxalic, glycolic, maleic, fumaric, succinic, tartaric, ascorbic, citric, malic, salicylic, lactic, benzoic, cinnamic, aspartic, glutamic, N-acetyl-aspartic or N-acetylglutamic acid as well as alkanesulfonic acids such as methanesulfonic acid or arenesulfonic acids, e.g. p-toluenesulfonic acid and the like, may be used.

The salt formation can be carried out e.g. in such a way that the corresponding acid is added to the solution of the compound of the formula (I) prepared in an inert solvent, e.g. ethanol, thereafter the salt formed is precipitated by adding preferably a water-immiscible organic solvent, e.g. diethyl ether.

For the preparation of quaternary ammonium salts a lower alkyl, alkenyl or benzyl halide or an alkyl sulfate may preferably be employed. The quaternization is suitably performed in an organic solvent such as acetone, acetonitrile, ethanol or their mixtures at a temperature range from room temperature up to the boiling point of the solvent.

The acid addition or quaternary ammonium salt obtained may be isolated e.g. by filtration and, when necessary, purified by recrystallization.

Conversely, the corresponding free bases can be liberated from their salts by an alkaline treatment.

The starting substances used in the process of the invention are partly known or can be prepared by using known methods.

The compounds of the formulae (IV), (V) and (VII) used as starting substances are novel and possess an own biological activity, too.

The compounds of the formula (III) may be prepared e.g. according to the following literature references: Ber. 55, 3406 (1922); Ann. Chem. 555, 80 (1952); GB patent specification No. 683,950; Yakugaku Zasshi 82, 1088 (1952); J. Chem. Soc. 4066 (1959); Coll. Czechoslov. Chem. Commun. 38, 3879 (1973).

The preparation of the compounds of the formula (II) is described in the Hungarian patent application No. 4092/89 filed concurrently with the Hungarian application on which the present application is based and the concurrently filed copending commonly assigned U.S. application Ser. No. 07/566,274.

The compounds of the formula (IV) can be prepared by the ethynylation reaction of suitably substituted 4-piperidone derivatives as described e.g. in the Hungarian patent specification No. 166,769 or in Farmaco (Pavia) Ed. Sci. 12, 34 (1957).

The carbamates of the formula (V) are obtained e.g. by reacting a compound of the formula (IV) with an isocyanate of the formula R-NCO, e.g. as described above.

The 2-oxo-1-oxa-8-azaspiro[4,5]decane derivatives of the formula (VII) can be prepared e.g. according to the process a) by reacting a suitably substituted compound of the formula (II) containing a methyl group as $R^1$ and a hydroxyl group as $R^2$, with a suitably substituted compound of formula (III).

The novel compounds of the formula (I) according to the invention and their salts exert a strong and selective dopaminergic action in the central nervous system: namely, they inhibit the central dopamine (hereinafter: DA) receptors in the cortical and subcortical brain regions and therefore, they possess antipsychotic effect. Thus, the compounds of the formula (I) are useful for the treatment of various psychiatric disorders such as acute and chronic schizophrenia, manic-depressive psychosis, agitations of various origin, psychomotor disquiet and other psychoses.

At present several in vivo methods are known for the investigation of inhibition of the cerebral DA receptors. One of these methods is based on the characteristic property of antipsychotic compounds that they are capable of inhibiting e.g. the behavioral forms induced in rats by apomorphine, which is a DA agonist. It has been proven in a number of studies and investigations that an excellent correlation exists between the in vivo inhibition of DA receptors measured in the apomorphine test and the clinical-therapeutic efficiency of antipsychotic compounds. Apomorphine induces a characteristic syndrome in rats and various animal species which manifests itself in the hyperactivity and stereotypic behavior of the animals (J. Pharm. Pharmacol. 19 627 (1957); J. Neurol. Transm. 40, 97 (1977); J. Psychiat. Res. 11, 1 (1974); J. Pharm. Pharmacol. 25, 1003 (1973); as well as Nature 263, 338 (1976)).

Male Hannover-Wistar rats weighing 160 to 180 g were used in these examinations. The test compounds were suspended in a 2% Tween 80 solution and diluted to the desired concentration by adding distilled water. The corresponding dose was administered to rats in a volume of 5 ml/kg. The control group was treated with the above solution containing no test substance.

One hour following the treatment with 2.5 mg/kg oral dose of the test compound, the rats were subcutaneously treated with 1 mg/kg of apomorphine hydrochloride.

15 minutes after administration of apomorphine, the animals were placed in a 5-channel behavior-observing device controlled by a microprocessor and the coordinated and stereotypic motion of the animals were measured for 15 minutes. Chlozapine (chemically 8-chloro-11-(4-methyl-1-piperazinyl)-5H-dibenzo[b,e][1,4]diazepine) was used in a dose of 2.5 mg/kg as reference drug. The results are shown as percentages of the control for both motion types.

Further on, the cataleptogenic (catalepsy-inducing) effect of the compounds was investigated by using the method of G. Stille and H. Launer [Arzneim.-Forsch. 21, 252 (1971)]. In these examinations male Wistar rats weighing 90 to 110 g were used which were orally treated by various doses of the test substances. The number of cataleptic animals was hourly registered for 6 hours following the treatment. An animal was considered to be cataleptic when it did not correct within 30 seconds its whimsical body position caused by lifting its upper limbs onto a horizontal rod set at a height of 8 cm. The $ED_{50}$ value was calculated from the percentage of cataleptic animals. The results are summarized in the Table.

The abbreviations used in the Table are as follows:
LMA: locomotor activity
n: number of animals
p.o.: oral administration
S.E.: standard error of the mean value
A: 8-[4,4-bis(4-fluorophenyl)-3-butenyl]-3-methyl-4-methylene-2-oxo-1-oxa-3,8-diazaspiro[4,5]decane
B: 8-[4,4-bis(4-fluorophenyl)-3-butenyl]-3-butyl-4-methylene-2-oxo-1-oxa-3,8-diazaspiro[4,5]decane

TABLE

| Compound | Inhibition of apomorphine-induced | | Cataleptogenic effect | |
|---|---|---|---|---|
| | LMA as percentage of the control | stereotypy | $ED_{50}$ mg/kg p.o. | n |
| A | −35 | −2 | 300 | 5 |
| B | −48 | +9 | 300 | 5 |
| Clozapine | −25 | +11 | 31.9 | 5 |

Control:
LMA: 100% (438.9 ± 54.7 sec ± S.E.)
Stereotypy: 100% (105.0 ± 13.7 sec ± S.E.)

It is obvious from the Table that a 2.5 mg/kg oral dose of the compounds of the formula (I) according to the invention decreased the apomorphine-induced locomotor hyperactivity with the same or a significantly higher efficiency than the reference drug did whereas, similarly to clozapine, they did not inhibit the stereotypy. Their cataleptogenic effect was at least ten times as favourable as that of the reference drug. Thus, it can be expected that the extrapyramidal side effects of the novel compounds of the formula (I) according to the invention would be less frequent or absent.

Due to their antipsychotic efficiency, the novel compounds of the formula (I) are useful for the systemic treatment of mammals, including man, suffering from a psychotic disease. Here the term "systemic treatment" means oral, rectal or parenteral administration. Depending on the severity of the disease and the condition of the patient the dose may be varied from 0.01 mg/kg to 40 mg/kg.

The compounds according to the invention can be converted into pharmaceutical compositions. These compositions may be administered orally, rectaly and/or parenterally. For oral administration, the composition may be formulated e.g. as a tablet, dragée or capsule. In order to prepare oral compositions, e.g. lactose or starch may be used as carriers. Gelatine, carboxymethylcellulose sodium, methylcellulose, polyvinylpyrrolidone or starch gum are suitable binding or granulating agents. As disintegrating agents mainly potato starch or microcrystalline cellulose may be added though ultraamylopectin or formaldehyde-casein and the like are also useful. Talc, colloidal silicic acid, stearin, calcium or magnesium stearate and the like are suitable anti-adhesive and sliding agents. Liquid oral compositions can be formulated e.g. as suspensions, syrups or elixirs which may contain water, glycols, oils, alcohols as well as coloring and flavoring agents.

Tablets may be prepared e.g. by compression following wet granulation. The mixture of the active ingredient with the carriers and optionally with a part of the disintegrating additive is granulated with an aqueous, alcoholic or aqueous-alcoholic solution of the binding agents in a suitable apparatus, then the granulate is dried. Subsequently, after mixing the other disintegrating, sliding and antiadhesive additives to the dried granulate, the mixture is compressed to tablets. If desired, the tablets may be provided with a groove in order to facilitate the administration. Tablets may also directly be prepared from a mixture containing the active ingredient and suitable additives. The tablets may optionally be converted to dragées by employing commonly used pharmaceutical additives, e.g. protective, flavoring or coloring agents such as sugar, cellulose derivatives (methyl- or ethylcellulose, carboxymethylcellulose sodium and the like), polyvinylpyrrolidone, calcium phosphate, calcium carbonate, food dyes, dyeing lacquers, aromatizing agents, iron oxide, pigments and the like. Encapsulated compositions are prepared by filling a mixture of the active ingredient with the additives into capsules.

For rectal administration, the composition of the invention is formulated as a suppository containing a carrier mass, the so-called "adeps pro suppositorio" in addition to the active ingredient. As carriers, vegetable fats such as hardened vegetable oils, or triglycerides of $C_{12-18}$ fatty acids (preferably the carriers bearing the trade name Witepsol) may be used. The active ingredient is uniformly distributed in the molten carrier mass, then suppositories are prepared by moulding.

For parenteral administration, the composition of the invention is formulated as an injectable solution. For preparing these injectable solutions, the active ingredients are dissolved in distilled water and/or various organic solvents, e.g. glycol ethers, if desired, in the presence of solubilizing agents such as polyoxyethylene sorbitan monolaurate or monooleate or monostearate (Tween 20, Tween 60 or Tween 80), respectively. The injectable solution may further contain various auxiliary agents, e.g. preservatives such as ethylenediamine tetraacetate as well as pH-modifying and buffering substances or, if desired, a local anaesthetic agent such as lidocaine. Before filling into the ampoules, the injectable solution containing the composition of the invention is filtered and after filling in, it is subjected to sterilization.

The invention also relates to a method for treating psychiatric diseases. This method comprises administering a therapeutically effective amount of an active ingredient of the formula (I) or a pharmaceutically acceptable acid addition salt or quaternary ammonium salt thereof to the patient.

The invention is illustrated in detail by the aid of the following non-limiting Examples.

EXAMPLE 1

Preparation of
8-[4,4-bis(4-fluorophenyl)-3-butenyl]-4-methylene-2-oxo-3-phenyl-1-oxa-3,8-diazaspiro[4,5]decane A mixture containing 8.4 g of 4-methylene-2-oxo-3-phenyl-1-oxa-3,8-diazaspiro[4,5]decane, 18.4 g of 4,4-bis(4-fluorophenyl)-3-butenyl chloride, 0.3 g of potassium iodide, 9.2 g of anhydrous potassium carbonate and 81 ml of methyl isobutyl ketone is mildly refluxed under argon while stirring for 12 hours. After cooling down and filtering off the inorganic salts, the precipitate is washed with methyl isobutyl ketone, the filtrate is washed with water to neutral, dried over anhydrous magnesium sulfate, then the solvent is evaporated under reduced pressure. After triturating the evaporation residue with n-hexane, the precipitate is filtered and recrystallized from ethanol to give the title compound in 83.5% yield, m.p.: 136.5°–137.5° C.

Analysis: Calculated for $C_{30}H_{28}F_2N_2O_2$: C 74.05; H 5.80; F 7.81; N 5.76%; found: C 74.19; H 5.85; F 7.74; N 5.83%.

EXAMPLE 2

Preparation of
8-[4,4-bis(4-fluorophenyl)-3-butenyl]-3-ethyl-4-methylene-2-oxo-1-oxa-3,8-diazaspiro[4,5]decane A mixture containing 7.8 g of 3-ethyl-4-methylene-2-oxo-1-oxa-3,8-diazaspiro[4,5]decane, 8.5 ml of anhydrous triethylamine, 80 ml of anhydrous methyl ethyl ketone, 0.3 g of potassium iodide and 16.7 g of 4,4-bis(4-fluorophenyl)-3-butenyl chloride is refluxed under nitrogen while stirring for 15 hours, then the solvent is distilled off under reduced pressure. After adding benzene and water to the residue, the benzene layer is washed with water to neutral, dried over anhydrous magnesium sulfate, filtered through an aluminum oxide bed and evaporated under reduced pressure. After recrystallizing the residue from ethanol, the title product is obtained in 68.7% yield, m.p.: 138°–139° C.

Analysis: Calculated for $C_{26}H_{28}F_2N_2O_2$: C 71.21; H 6.44; F 8.66; N 6.39%; found: C 71.32; H 6.46; F 8.75; N 6.58%.

EXAMPLE 3

Preparation of
8-(3,3-diphenyl-2-propenyl)-3-methyl-4-methylene-2-oxo-1-oxa-3,8-diazaspiro[4,5]decane 9.4 g of 1-(3,3-diphenyl-2-propenyl)-4-ethynyl-4-methylcarbamoyloxypiperidine are refluxed in 100 ml of 0.05 mol/liter ethanolic sodium ethoxide solution under argon for 3 hours. After cooling down, the alkoxide is decomposed by adding aqueous ammonium chloride solution and the solvent is distilled off under reduced pressure. After adding benzene and water to the residue, the benzene layer is separated and dried, then evaporated under reduced pressure. After recrystallizing the solid evaporation residue from ethanol, the title compound is obtained in 71.7% yield, m.p.: 126°–127° C.

Analysis: Calculated for $C_{24}H_{26}N_2O_2$: C 76.97; H 7.00; N 7.48%; found: C 77.18; H 6.81; N 7.58%.

The following compound is prepared according to Example 3:
8-(3,3-diphenyl-2-propenyl)-3-isopropyl-4-methylene-2-oxo-1-oxa-3,8-diazaspiro[4,5]decane, m.p. 131°–132° C.

EXAMPLE 4

Preparation of
8-[4,4-bis(4-fluorophenyl)-3-butenyl]-3-cyclohexyl-4-methylene-2-oxo-1-oxa-3,8-diazaspiro[4,5]decane 20.4 g of 8-[4,4-bis(4-fluorophenyl)-3-butenyl]-3-cyclohexyl-4-hydroxy-4-methyl-2-oxo-1-oxa-3,8-diazaspiro[4,5]decane are boiled with 1.52 g of p-toluenesulfonic acid monohydrate in 204 ml of xylene while stirring in an apparatus fitted with a water-trap and azeotropically distilling off the water formed in the reaction. After the termination of the reaction (about 2 hours) the reaction mixture is cooled down and its pH value is adjusted to 9–10 by adding 5% by weight aqueous sodium hydroxide solution. Then, the organic phase is washed with water to neutral, dried over anhydrous sodium sulfate and evaporated under reduced pressure. After recrystallizing the residue from a mixture of benzene and ethanol, the title product is obtained in 90.3% yield, m.p.: 145°–146° C.

Analysis: Calculated for $C_{30}H_{34}F_2N_2O_2$: C 73.15; H 6.96; F 7.71; N 5.69%; found: C 73.30; H 7.18; F 7.60; N 5.77%.

The following compounds are prepared according to the preceding Example:
8-[4,4-bis(4-fluorophenyl)-3-butenyl]-3-decyl-4-methylene-2-oxo-1-oxa-3,8-diazaspiro[4,5]decane, m.p.: 50°–51° C.;
8-[3,3-bis(4-fluorophenyl)-2-propenyl]-3-isopropyl-4-methylene-2-oxo-1-oxa-3,8-diazaspiro[4,5]decane, m.p.: 137°–138° C.; and
8-[4,4-bis(4-fluorophenyl)-3-butenyl]-3-[2-(3,4-dimethoxyphenyl)ethyl]-4-methylene-2-oxo-oxa-3,8-diazaspiro[4,5]decane, m.p.: 88°–90° C.

EXAMPLE 5

Preparation of
8-[4,4-bis(4-fluorophenyl)-3-butenyl]-4-methylene-3-(1-naphthyl)-2-oxo-1-oxa-3,8-diazaspiro[4,5]decane A mixture containing 11.0 g of 1-[4,4-bis(4-fluorophenyl)-3-butenyl]-4-ethynyl-4-hydroxypiperidine, 6.0 g of 1-naphthyl isocyanate, 0.2 g of anhydrous potassium acetate and 36 ml of C-picoline is refluxed under nitrogen while stirring for 5 hours. After evaporating the solvent under reduced pressure, the residue is taken up in benzene, filtered through an aluminum oxide column and then evaporated under reduced pressure. The residue is recrystallized from methanol under clarifying by activated carbon to give the title product in 76.5% yield, m.p.: 99°–101° C.

Analysis: Calculated for $C_{34}H_{30}F_2N_2O_2$: C 76.10; H 5.63; F 7.08; N 5.22%; found: C 76.23; H 5.76; F 7.13; N 5.25%.

By using the appropriate starting substances the following compound is prepared analogously to the preceding Example:
8-[4,4-bis(4-fluorophenyl)-3-butenyl]-3-isopropyl-4-methylene-2-oxo-1-oxa-3,8-diazaspiro[4,5]decane, m.p.: 135°–136° C.

EXAMPLE 6

Preparation of
8-[4,4-bis(4-fluorophenyl)-3-butenyl]-3-(4-chlorophenyl)-4-methylene-2-oxo-1-oxa-3,8-diazaspiro[4,5]-decane A solution containing 5.8 g of 4-acetyl-1-[4,4-bis(4-fluorophenyl)-3-butenyl]-4-hydroxypiperidine and 7.0 g of 4-chlorophenyl isocyanate in 30 ml of tripropylamine is gently refluxed under argon while stirring for 3 hours, then the solvent is distilled off under reduced pressure. After adding benzene to the residue and filtering off the insoluble part, the benzene filtrate is filtered through a silica gel bed and evaporated under reduced pressure. The solid evaporation residue is recrystallized from ethanol under clarifying by activated carbon to obtain the title compound in 52% yield, m.p.: 186°–188° C.

Analysis: Calculated for $C_{30}H_{27}ClF_2N_2O_2$: C 69.16; H 5.22; Cl 6.80; F 7.29; N 5.38%; found: C 69.17; H 5.38; Cl 6.73; F 7.11; N 5.55%.

EXAMPLE 7

Preparation of
8-[4,4-bis(4-fluorophenyl)-3-butenyl]-3-n-butyl-4-methylene-2-oxo-1-oxa-3,8-diazaspiro[4,5]decane A mixture containing 8.2 g of 8-[4,4-bis(4-fluorophenyl)-3-butenyl]-4-methylene-2-oxo-1,3-dioxa-8-azaspiro[4,5]decane, 25 ml of xylene and 2.0 ml of butylamine is stirred at room temperature for 18 hours, then 0.8 g of p-toluenesulfonic acid monohydrate and 70 ml of xylene are added and the reaction mixture is boiled while azeotropically distilling off the water formed in the reaction. After termination of the reaction which is observed by thin layer chromatography (TLC), the mixture is cooled down and made alkaline to a pH of 9 to 10 by adding 5% by weight aqueous sodium hydroxide solution. After washing the organic phase with water to neutral and drying over anhydrous magnesium sulfate, the solvent is distilled off under reduced pressure. The crude product obtained as evaporation residue is recrystallized from ethanol under clarifying by activated carbon to give the title product in 72.5% yield, m.p.: 92°–93° C.

Analysis: Calculated for $C_{28}H_{32}F_2N_2O_2$: C 72.08; H 6.91; F 8.14; N 6.00%; found: C 72.00; H 7.14; F 8.30; N 5.81%.

By using the appropriate starting substances the following compound is prepared analogously to the preceding Example:
8-[4,4-bis(4-fluorophenyl)-2-propenyl]-4-methylene-2-oxo-3-propyl-1-oxa-3,8-diazaspiro[4,5]decane, m.p.: 128°–129° C.

EXAMPLE 8

Preparation of
8-[4,4-bis(4-fluorophenyl)-3-butenyl]-8-methyl-4-methylene-2-oxo-3-propyl-1-oxa-3,8-diazaspiro[4,5decane-8-ium iodide 4.0 g of 8-[4,4-bis(4-fluorophenyl)-3-butenyl]-4-methylene-2-oxo-3-propyl-1-oxa-3,8-diazaspiro[4,5]decane are boiled under reflux with 0.7 ml of methyl iodide in 40 ml of methyl isobutyl ketone for 2 hours. After cooling down, the crystalline precipitate is filtered, washed with diisopropyl ether, cooled to 0° C. and dried to obtain 92.2% yield of the title quaternary ammonium salt, m.p.: 244°–245° C.

EXAMPLE 9

Preparation of
8-(3,3-diphenyl-2-propenyl)-4-methylene-2-oxo-3-propyl-1-oxa-3,8-diazaspiro[4,5]decane 12.6 g of 8-(3,3-diphenyl-2-propenyl)-4-hydroxy-4-methyl-2-oxo-3-propyl-1-oxa-3,8-diazaspiro[4,5]decane are refluxed in a mixture of 126 ml of acetic acid and 5.7 ml of acetic anhydride under nitrogen while stirring for 4 to 5 hours, then the solvent is distilled off under reduced pressure. The residue is made alkaline by adding 5% by weight aqueous sodium hydroxide solution and extracted with benzene. After washing the benzene phase with water to neutral and drying over anhydrous sodium sulfate, benzene is evaporated under reduced pressure and the remaining crude product is recrystallized from ethanol to give the title compound in 85.7% yield, m.p.: 126°–127° C.

Analysis: Calculated for $C_{26}H_{30}N_2O_2$: C 77.58; H 7.51; N 6.96%; found: C 77.59; H 7.68; N 7.12%.

EXAMPLE 10

Preparation of
8-[4,4-bis(4-chlorophenyl)-3-butenyl]-3-butyl-4-methylene-2-oxo-1-oxa-3,8-diazaspiro[4,5]decane 10.7 g of 4,4-bis(4-chlorophenyl)-3-butenyl bromide are added to the solution of 4.5 g of 3-butyl-4-methylene-2-oxo-1-oxa-3,8-diazaspiro[4,5]decane in 45 ml of acetone containing 4.20 g of anhydrous potassium carbonate and 0.5 g of potassium iodide. The heterogeneous reaction mixture is refluxed under nitrogen while stirring for 5 hours. After evaporating the solvent under reduced pressure, water is added to the residue and extracted with benzene. The benzene phase is washed with water until halide-free, filtered through a silica gel bed and evaporated under reduced pressure. The residue is recrystallized from ethanol to give the title product in 79.0% yield, m.p.: 110°–111° C.

Analysis: Calculated for $C_{28}H_{32}Cl_2N_2O_2$: C 67.33; H 6.46; Cl 14.20; N 5.61%; found: C 67.50; H 6.44; Cl 14.25; N 5.80%.

By using appropriate starting substances the following compounds are prepared analogously to the preceding Example:
8-[4,4-bis(4-fluorophenyl)-3-butenyl]-3-methyl-4-methylene-2-oxo-1-oxa-3,8-diazaspiro[4,5]decane, m.p.: 127.5°–128.5° C.;
8-[3-(4-acetyloxyphenyl)-3-(3-trifluoromethylphenyl)-2-propenyl]-4-methylene-2-oxo-3-phenyl-1-oxa-3,8-diazaspiro[4,5]decane (E:Z=1:1), m.p.: 124°–126° C.;
8-[3,3-bis(4-fluorophenyl)-2-propenyl]-3-butyl-4-methylene-2-oxo-1-oxa-3,8-diazaspiro[4,5]decane, m.p.: 132.5°–134° C.;
(E)-8-[3-(acetyloxyphenyl)-3-(3-trifluoromethylphenyl)-2-propenyl]-3-cyclohexyl-4-methylene-2-oxo-1-oxa-3,8-diazaspiro[4,5]decane, m.p.: 177°–178° C.;
8-[3,3-bis(3,5-dichlorophenyl)-2-propenyl]-3-methyl-4-methylene-2-oxo-1-oxa-3,8-diazaspiro[4,5]decane, m.p.: 141°–143° C.;
(E)-8-[3-(4-acetyloxyphenyl)-3-(3-trifluoromethylphenyl)-2-propenyl]-4-methylene-2-oxo-3-propyl-1-oxa-3,8-diazaspiro[4,5]decane, m.p.: 111°–112° C.;
3-butyl-8-(3,3-diphenyl-2-propenyl)-4-methylene-2-oxo-1-oxa-3,8-diazaspiro[4,5]decane, m.p.: 138°–139° C.;

3-benzyl-8-[4,4-bis(4-fluorophenyl)-3-butenyl]-4-methylene-2-oxo-1-oxa-3,8-diazaspiro[4,5]decane, m.p.: 78°–79° C.;

8-[4,4-bis(4-fluorophenyl)-3-butenyl]-3-tert-butyl-4-methylene-2-oxo-1-oxa-3,8-diazaspiro[4,5]decane, m.p.: 109°–110° C.;

8-[4,4-bis(4-fluorophenyl)-2-propenyl]-3-methyl-4-methylene-2-oxo-1-oxa-3,8-diazaspiro[4,5]decane, m.p.: 141°–142° C.;

8-[4,4-bis(4-fluorophenyl)-3-butenyl]-4-methylene-2-oxo-3-propyl-1-oxa-3,8-diazaspiro[4,5]decane, m.p.: 130°–131° C.;

8-[4,4-bis(4-chlorophenyl)-3-butenyl]-3-methyl-4-methylene-2-oxo-1-oxa-3,8-diazaspiro[4,5]decane, m.p.: 136°–137° C.; and 3-benzyl-8-[4,4-bis(4-chlorophenyl)-3-butenyl[-4-methylene-2-oxo-1-oxa-3,8-diazaspiro[4,5]decane, m.p.: 138°–139° C.

EXAMPLE 11

Preparation of 8-[4,4-bis(4-fluorophenyl)-3-butenyl]-4-methylene-2-oxo-1,3-dioxa-azaspiro[4,5]decane After introducing dry gaseous hydrogen chloride into a solution of 32.0 g of 1-[4,4-bis(4-fluorophenyl)-3-butenyl]-4-butylcarbamoyloxy-4-ethynylpiperidine in 160 ml of anhydrous dioxane at 15° to 20° C. for 2.5 to 3 hours, the reaction mixture is left to stand overnight. After evaporating the solvent under reduced pressure at 40° to 50° C., water is added to the residue and the crystalline product is filtered off. This hydrochloride precipitate is suspended in water, the base is liberated by adding sodium hydrogen carbonate and extracted into benzene. After drying over anhydrous sodium sulfate, the benzene solution is evaporated under reduced pressure on a water bath of 40° C. The evaporation residue is recrystallized from a mixture of diisopropyl ether and hexane under clarifying by activated carbon to give the title product in 84.4% yield, m.p.: 70.5°–72° C.

Analysis: Calculated for $C_{24}H_{23}F_2NO_3$: C 70.06; H 5.63; F 9.24; N 3.40%; found: C 70.23; H 5.80; F 9.33; N 3.38%.

EXAMPLE 12

The new compounds according to the invention can be converted e.g. to the following pharmaceutical compositions.

a) Preparation of Tablets 50.0 g of active ingredient are mixed together with 92 g of lactose, 40 g of potato starch, 4 g of polyvinylpyrrolidine, 6 g of talc, 1 g of magnesium stearate, 1 g of colloidal silicon dioxide (Aerosil) and 6 g of ultraamylopectin and, after wet granulation, the product obtained is compressed to tablets containing 50 mg of the active ingredient each.

b) Preparation of Dragées

After coating the tablets prepared as described above in a known manner with a layer comprising sugar and talc, the dragées obtained are polished with a mixture of bee wax and carnauba wax to obtain dragées weighing 250 mg each.

c) Preparation of Capsules 100 g of active ingredient are thoroughly mixed together with 30 g of sodium lauryl sulfate, 280 g of starch, 280 g of lactose, 4 g of colloidal silicon dioxide (Aerosil) and 6 g of magnesium stearate, then the mixture is sieved and filled into hard gelatine capsules to obtain capsules containing 100 mg of active ingredient each.

d) Preparation of Suppositories (Note: all weights are calculated for one suppository)
100.0 mg of active ingredient are thoroughly mixed together with 200.0 mg of lactose, 1700.0 mg of suppository base (e.g. Witepsol 4) are molten, cooled to 35° C. and the mixture of the active ingredient and lactose is mixed thereto by using a homogenizer. The product obtained is poured into cooled conic moulds. Each suppository weighes 2000 mg.

e) Preparation of a Suspension

| Components in 100 ml of the suspension: | |
|---|---|
| Active ingredient | 1.00 g |
| Sodium hydroxide | 0.26 g |
| Citric acid | 0.30 g |
| Nipagin (methyl 4-hydroxybenzoate sodium salt) | 0.10 g |
| Carbapol 940 (polyacrylic acid) | 0.30 g |
| 96% Ethanol | 1.00 g |
| Raspberry flavor | 0.60 g |
| Sorbitol (Aqueous solution of 70%) | 71.00 g |
| Distilled water up to | 100.00 ml |

After adding Carbopol in little portions to the solution of Nipagin and citric acid in 20 ml of distilled water under vigorous stirring, the solution obtained is allowed to stand for 10 to 12 hours. Subsequently, the amount given above of sodium hydroxide dissolved in 1 ml of distilled water, the aqueous solution of sorbitol and finally the ethanolic solution of the raspberry flavor are dropped in under stirring. The active ingredient is added in small portions to this mixture and suspended by using a submerged homogenizer. Finally, the suspension is supplemented to 100 ml by adding distilled water and the syrupy suspension is led through a colloid mill.

We claim:

1. A compound of the Formula (I),

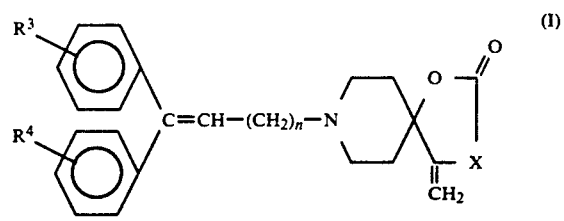

wherein

X means oxygen or an >NR group, wherein

R stands for hydrogen, $C_{1-12}$alkyl, $C_{3-6}$cycloalkyl, carbocyclic $C_{6-10}$aryl or carbocyclic $C_{6-10}$aryl $C_{1-4}$alkyl group, the latter two being unsubstituted or substituted on their aromatic moiety by at least one same or different halogen, $C_{1-4}$alkyl group or $C_{1-4}$alkoxy group;

$R^3$ and $R^4$, which are the same or different, represent hydrogen, or at least one halogen, $C_{1-4}$alkyl, $C_{1-4}$alkoxy, trihalomethyl group or hydroxyl group free or esterified by a $C_{1-4}$alkanoic acid; and n is 1 or 2, or an isomer, solvate, hydrate, or pharmaceutically acceptable acid addition or quaternary ammonium salt thereof.

2. 8-[4,4-bis(4-fluorophenyl)-3-butenyl]-3-methyl-4-methylene-2-oxo-1-oxa-3,8-diazaspiro[4,5]decane, or an isomer, solvate, hydrate or pharmaceutically acceptable acid addition or quaternary ammonium salt thereof as defined in claim 1.

3. 8-[4,4-bis(4-fluorophenyl)-3-butenyl]-3-butyl-4-methylene-2-oxo-1-oxa-3,8-diazaspiro[4,5]decane, or an isomer, solvate, hydrate or pharmaceutically acceptable acid addition or quaternary ammonium salt thereof as defined in claim 1.

4. A compound defined in claim 1 and selected from the group consisting of:
8-{4,4-bis(4-fluorophenyl)-3-butenyl}-3-butyl-4-methylene-2-oxo-1-oxa-3,8-diazaspiro{4,5}decane,
3-benzyl-8-{4,4-bis(4-fluorophenyl)-3-butenyl}-4-methylene-2-oxo-1-oxa-3,8-diazaspiro{4,5}decane,
8-{4,4-bis(4-fluorophenyl)-3-butenyl}-4-methylene-2-oxo-1,3-dioxa-8-azaspiro(4,5)decane, and
8-{4,4-bis(4-fluorophenyl)-3-butenyl}-3-methyl-4-methylene-2-oxo-1-oxa-3,8-diazaspiro{4,5}decane, or an isomer, solvate, hydrate or pharmaceutically acceptable acid addition or quaternary ammonium salt thereof.

5. A pharmaceutical composition for treating acute and chronic schizophrenia, manic depressive psychosis, agitation and psychomotor disquiet, which comprises as active ingredient a therapeutically effective amount of a Compound of the Formula I as defined in claim 1, or a pharmaceutically acceptable acid addition or quaternary ammonium salt thereof in admixture with a pharmaceutically acceptable inert carrier.

6. A method for the treatment of acute and chronic schizophrenia, manic depressive psychosis, agitation and psychomotor disquiet, which comprises administering to a mammalian subject to be treated a therapeutically effective amount of a compound of the Formula (I) as defined in claim 1, or a pharmaceutically acceptable acid addition or quaternary ammonium salt thereof alone or in the form of a pharmaceutical composition.

* * * * *